United States Patent
Selman et al.

(10) Patent No.: US 8,132,452 B1
(45) Date of Patent: Mar. 13, 2012

(54) METHOD FOR SAMPLING FLUID FROM A WELL WITH A GAS TRAP

(75) Inventors: Thomas H. Selman, Midland, TX (US); Juanita C. Selman, Midland, TX (US); Matthew J. Jennings, Midland, TX (US); Richard James Gonzales, Midland, TX (US); Brian A. Jennings, Midland, TX (US); Stephen M. Bergman, Casper, WY (US)

(73) Assignee: Selman and Associates, Ltd, Midland, TX (US)

( * ) Notice: Subject to any disclaimer, the term of this patent is extended or adjusted under 35 U.S.C. 154(b) by 317 days.

(21) Appl. No.: 12/615,634

(22) Filed: Nov. 10, 2009

(51) Int. Cl.
*E21B 49/08* (2006.01)
*E21B 44/00* (2006.01)

(52) U.S. Cl. .............. 73/152.23; 166/250.01; 166/264; 175/50; 175/58

(58) Field of Classification Search .............. 73/152.23, 73/36, 863; 166/250.01, 264, 105.5, 316; 175/40, 58, 50
See application file for complete search history.

(56) References Cited

U.S. PATENT DOCUMENTS

| | | | | |
|---|---|---|---|---|
| 2,752,776 A | * | 7/1956 | Sixt et al. | 73/36 |
| 2,752,777 A | * | 7/1956 | Jacobs et al. | 73/36 |
| 4,831,559 A | * | 5/1989 | Miller | 73/36 X |
| 5,869,343 A | * | 2/1999 | Handschuck et al. | 73/36 X |
| 7,844,400 B1 | * | 11/2010 | Selman et al. | 166/264 X |
| 7,957,903 B1 | * | 6/2011 | Selman et al. | 166/264 X |
| 2007/0050154 A1 | * | 3/2007 | Albahri | 702/22 |

* cited by examiner

*Primary Examiner* — Thomas P Noland
(74) *Attorney, Agent, or Firm* — Buskop Law Group, PC; Wendy Buskop (57) ABSTRACT

A low maintenance adjustable method for sampling fluid from a well using a gas analyzer, a fluid conditioner, and a gas trap. The gas trap can have a plurality of couplings, a plurality of hammer unions, a plurality of base manifold pipes, a base manifold flow line, a chimney pipe connected to the base manifold flow line, a controllable valve, a reducer connected to the chimney, an expansion chamber component connected to the reducer, a restrictor mounted to the expansion chamber component, and a conduit connection connected to the restrictor for engaging a conduit to flow a gas sample from the gas trap to a gas analyzer.

28 Claims, 11 Drawing Sheets

- USING THE LOCATION PROCESSOR AND COMPUTER INSTRUCTIONS ON THE LOCATION DATA STORAGE TO PROVIDE AN ALARM TO HANDS PROXIMATE TO THE FLOW LINE WHEN CONCENTRATIONS OF COMPONENTS OF FLUID FROM THE FLOW LINE EXCEED PRESET LIMITS — 840

- USING A CLIENT DEVICE HAVING A CLIENT PROCESSOR AND CLIENT DATA STORAGE FOR RECEIVING, VIEWING AND STORING ANALYSIS INFORMATION; WHEREIN THE CLIENT DEVICE IS IN COMMUNICATION WITH THE NETWORK — 842

- USING THE LOCATION PROCESSOR AND COMPUTER INSTRUCTIONS ON THE LOCATION DATA STORAGE TO BROADCAST ANALYSIS INFORMATION TO A MEMBER OF THE GROUP CONSISTING OF: DISPLAYS NEAR HANDS PROXIMATE TO THE FLOW LINE; CLIENTDEVICES ASSOCIATED WITH EACH OF THE HANDS; CLIENT DEVICES ASSOCIATED WITH FIRST RESPONDERS; CLIENT DEVICES ASSOCIATED WITH AT LEAST ONE USER ASSOCIATED WITH THE FLUID OF THE FLOW LINE; OR COMBINATIONS THEREOF — 844

- USING A FOUR WAY VALVE DISPOSED ON THE GAS TRAP TO ACTUATE BETWEEN AN "ON" AND AN "OFF" POSITION — 846

- USING A COMPRESSED AIR SOURCE IN FLUID COMMUNICATION WITH THE FOUR WAY VALVE TO PROVIDE AIR TO THE GAS TRAP — 848

- USING AN ELECTRONIC RELAY IN COMMUNICATION WITH THE FOUR WAY VALVE FOR ACTUATING THE FOUR WAY VALVE BETWEEN THE "ON" AND "OFF" POSITIONS — 850

- USING A CLIENT DEVICE IN COMMUNICATION WITH THE ELECTRONIC RELAY TO REMOTELY ACTUATE THE FOUR WAY VALVE BETWEEN THE "ON" AND "OFF" POSITIONS — 852

FIGURE 8D

METHOD FOR SAMPLING FLUID FROM A WELL WITH A GAS TRAP

FIELD

The present embodiments generally relate to a method for sampling gas, vapor, and gas/liquid mixtures from a natural gas well, an oil well or another well that emits at least a gas using a gas trap.

BACKGROUND

A need exists for a method for use with natural gas wells, oil wells, and other wells that emit at least some gas or vapor that can handle high pressure gas streams while simultaneously enabling a quick accurate analysis of a homogenous mix of the emitted fluid stream.

A need exists for a method that enables workers proximate to a drilling site to be immediately aware of the presence of a combustible gas, such as hydrogen and take precautions to prevent explosions or the loss of life.

A further need exists for a method for sampling gas and vapor which uses a modular gas trap that is easy to manufacture, to repair, and to install in the field.

A need exists for a gas analysis method with a gas trap that is strong, is able to stand up independently, and is able to withstand physical impacts in the field.

A need exists for a gas method that can be monitored remotely in areas with terrorist activity, such as Iraq, to reduce potential for human harm at a remote and dangerous location.

The present embodiments meet these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present method in detail, it is to be understood that the method is not limited to the particular embodiments and that it can be practiced or carried out in various ways.

The present embodiments relate to a method of sampling gas from a well, such as a natural gas well, during drilling, that is safer than known techniques.

The present embodiments further provide a method for monitoring conditions locally, remotely, or both simultaneously at a well that enables fluid from the well to be captured at a flash point so that there is no need to mechanically separate or filter the fluid from the well prior to any gas analysis. The well can be a new well or a workover well. The gas can be analyzed for example with a chromatograph or other similar gas analyzer.

The fluid coming from the well can the fluid from the fluid conduit, which can also be referred to herein as "the flow line", from a well being drilled, such as a natural gas well, a water well, an oil well, or a similar type of well.

The gas components can be determined during the gas analysis. The gas components can be logged with well data using a processor of a computer that is in communication with the gas analyzer. The logged gas components along with the well data can be used to determine if the well bore drilling is performing according to predetermined values. Well data can include well pressure, well temperature, and other measurable or identifiable well conditions. Predetermined values can include geologically predefined goals.

Embodiments of the gas analysis method allow a drilling crew to be aware of combustible gas that could ignite at a drilling site by enabling continuous sampling of gas coming from the well using a gas trap that has only one valve as a moving part.

The present method enables samples of fluid to be taken through an installed device, such as a gas trap, removably connectable to the flow line of a drilling well.

The method not only captures a sample of fluid from a well, such as a gas, at a point of being homogenously mixed, but also conditions the sampled fluid including removing moisture. The sample can be passed to a conditioner for removal of water and particulate from the gas sample.

The method can then pass the conditioned sample to a gas analyzer continuously and safely with the results of the gas analysis being immediately viewable by local workers or transmittable through one or more networks with at least one processor and a web server, for simultaneous remote monitoring and alarming.

The gas analyzer can compare the sample of gas to known gas properties which can be stored in data storage of the gas analyzer. The processor of the gas analyzer can not only use the data of the data storage to compare the sample of gas to known concentrations and properties, but the processor associated with the gas analyzer can also have computer instructions for alerting a local crew to the presence of several conditions during drilling. A condition being monitored for can be the presence and detection of a combustible gas.

The method can use the gas trap, the conditioner, and the gas analyzer in series, can continuously monitor for the presence of a combustible gas and can provide an alarm to the crew to take safety precautions, for example by reducing the presence of open flames.

By providing an alarm or other notice from the processor associated with the gas analyzer, the crew is allowed to employ proper safety procedures to compensate for combustible gas on a drill site, thus potentially saving lives which could be lost if the flow line explodes or if the crew is allowed to remain unaware of the presence of the combustible gas.

In embodiments of the method, batch samples are not taken, but rather, continuous sampling or collecting, continuous conditioning, and continuous analyzing is performed.

Another condition that can be monitored by the method is the condition in drilling known as "over-pressurizing." The method, using the samples of gas, the conditioner, and the gas analyzer, can continuously monitor samples from the gas trap when overpressure zones are detected. The crew can then change the mixture of the drilling muds and change rates of flow of drilling muds to a well, thereby eliminating the overpressure zones. The method with continuous monitoring by a gas analyzer can monitor for other conditions as well.

Embodiments enable a gas analyzer to consistently, constantly, and continuously, predict potential overpressure zones that are about to be encountered during drilling.

Overpressure zones are a serious safety problem during drilling. Other known sampling methods, using gas traps which are very large, do not provide for continuous homogenous sampling at the flash point of the sample in the flow conduit or for continuously using a gas trap with little to no moving parts. The method dramatically improves the reliability of continuous sampling from a well, enabling prediction of overpressure zones in less than three minutes.

The method can collect, with the unique gas trap, a homogenous mixture of the fluid being drilled.

The method is able to sample gas in a fluid line at a point of high agitation in the flow stream from the well, at which point a highly accurate predictive sample is formed.

The method of the invention enables the components being detected to truly represent the entire mixed stream, and not just a portion of the stream, due to the sampling at the flash point and at a point of high agitation of the fluid in the stream from the well.

The stream is accurately represented by the sample from the gas trap because of the location of the gas trap in the fluid conduit line at the flash point, and because the gas trap can endure and step down the pressures of the fluid from the flow line to a test pressure for safe sampling. Therefore, it is not necessary to apply theoretical models to the results of this sample analysis to theorize the correct component mix of the stream.

The method can sample fluid from a well being drilled. The fluid can be a liquid/gas mixture, a vapor/gas mixture, a mixture of gases, a particulate and gas mixture, or combinations thereof.

The method can use a modular gas trap. The gas trap can be formed from connected segments that can be threaded together so that there is no need in the field to weld the components together. The gas trap can have segments including union hammers and conduit connectors that are independently removable in the field for maintenance.

The gas trap usable in the method can be a small and lightweight gas trap with a height of less than twelve feet. The gas trap can weigh less than 80 pounds, providing a method that can be easily lifted and installed by two men.

The gas trap usable in the method can be portable. It is contemplated that the gas trap can be moved easily in a pick-up truck, requiring no road permits, no special 18 wheel flat bed, and no other special treatment. The gas trap can be easy to install, requiring no special operator training.

The method can contemplate that the gas trap can be constructed from steel. Using a steel gas trap enables the gas trap to handle a variety of pressures while being continuously reliable.

In embodiments, a gas trap can have little to no moving parts, other then one valve for installation. The method contemplates using a gas trap that can be left continuously open, during sampling, so that during sampling there are no motors needed.

The method can use a "stair step" gas trap, which can have an open flow steel design, which resists deformation in the field during use due to high pressure.

The method can be a "no humans needed" or a "hands free" method that is low maintenance, or requires no maintenance to use, and can be monitored either remotely or locally. No on-site user is needed to run the gas trap of the method. Having a method requiring no on-site user is significant when a well is experiencing bad weather, such as a hurricane. In the Gulf Coast area of the United States, there are many wells that need to keep operating during bad weather. The method enables continued operation in bad weather when humans might otherwise risk their lives or be subject to injury.

The gas trap can be made from a dual component tubular. The dual component tubular can be a tubular with a sheath providing two different properties to the material, such as impact resistance and resistance to internal pressure deformation.

Embodiments can include a cathodic material on the outside of the gas trap to enhance resistance to degradation due to natural elements. The gas trap can include a coating on the gas trap that resists attracting lightening. The gas trap can have a high impact resistance and a high durometer value.

In embodiments, the gas trap usable in the method can stand from about 6 feet to about 12 feet in height, can be able to stand on its own weight with a stable base, and will not break apart during serious natural conditions such as a hurricane or a minor earthquake.

Operationally, the gas trap usable in the method is not dependent on the fluid level in the flow line, as opposed to customary motor driven gas traps located in the pits or a shale shaker. The gas trap usable in the method can pull samples when the fluid in the flow line is ½ full, ¼ full or 90 percent full without needing another device to "feed" the gas trap.

Operationally, the method requires no "pre-filtering" of the flow line fluid before acceptance of the fluid into the gas trap. Fluid can come directly into the gas trap from the flow line without any form of pretreatment.

The gas trap can connect to the top of a flow line, and because of its ability to connect at this point, the gas trap is safer than other gas traps because it is less likely to fall on the heads of workers in the pit, which enables a safer operating environment for the drilling hands.

The method provides geological benefits because it can operate at a strategic location of natural agitation in the flow line, allowing a good representation for taking the sample showing a truly mixed fluid stream and subsequent analysis.

Embodiments of the method can provide an emergency shut off for safety, which can be a safety relief valve.

The method can use a gas trap that provides a decompression point in the gas trap, allowing to fluid to flow while air drilling, enabling logging of the whole well without needing to change out equipment.

The gas trap can include a plurality of couplings for attaching to the flow of a drilling rig or a well. The couplings can be secured in parallel along the flow line, forming a first part of a base manifold for the gas trap.

Attached to each of the couplings can be hammer unions. A base manifold pipe can fluidly connect to each of the hammer unions.

A base manifold flow line can connect to each of the base manifold pipes, thereby completing the formation of the base manifold. The base manifold flow line can flow the fluid from each of the couplings, the hammer unions, and the base manifold pipes to a single chimney pipe. In embodiments, the base manifold flow line can be C-shaped, connecting to one of the base manifold pipes at one end of the C-shape, connecting to the base manifold pipes at the other end of the C-shape, and connecting to a third base manifold pipe at a central point between the two end couplings.

It is contemplated that the gas trap can work using a base manifold with more than three couplings and associated parts. For example, the base manifold can have six couplings if the flow line is large, such as a flow line with a four foot diameter wherein the pressure is over 1000 psi in the flow line. In embodiments, the flow line can be four inches in diameter and the coupling can be two inches in diameter.

The chimney pipe can include a controllable valve. The controllable valve can be used during installation and removal of the gas trap. The controllable valve can be in the center of the chimney pipe or can be near the top or near the bottom of the chimney pipe. The chimney pipe can be a one piece conduit, or can be formed from a plurality of segments of conduit for ease of installation in an area with rocky overhangs or other equipment interfering with the gas trap. The controllable valve can be a ball valve.

A connector, such as a T-connector, can be integral with the chimney pipe and can provide the components that allow a safety release of the gas from the gas trap. A quick release coupling can be used with the T-connector as the safety release.

A reducer can be attached to the chimney pipe for modifying the diameter of the fluid flow connected from the chimney pipe.

Fluid, which can be air, an air and gas mixture, or mixtures with steam, can flow from the reducer to an expansion chamber component. From the expansion chamber component, a restrictor, which can be an S-shaped restrictor with a diameter no more than one third the diameter of the expansion chamber component, can be used to lower pressure and to clean the fluid.

A conduit connection can engage the restrictor, which can have a shape other than an S, such as two connected C-shapes, or two connected U-shapes. The conduit connection can engage a conduit that flows the gas sample to a gas analyzer.

In embodiments, the gas trap can include a reference gas injector. The reference gas injector can connect to one of the base manifold pipes. The reference gas injector inserts, typically under pressure, a reference gas of known specification to the gas analyzer into the base manifold pipe. When the reference gas comes through the gas trap to the gas analyzer, from the gas analyzer through a connected processor, or directly from the gas analyzer, a signal can be generated through a network to a client device remotely providing information. The information can be information on whether or not the gas trap is clogged or if the gas trap is working properly.

Analysis of the time and pressure of a gas sample can be compared to the time it takes for the gas analyzer to identify the reference gas, and the comparison can indicate if particulate has clogged the gas trap. This remote analysis and monitoring is an important feature, as the gas trap maintenance personnel can quickly go into the field and fix the gas trap, or they can call a hand nearby the gas trap to open the safety relief valve to ensure safe operation until the gas trap problem can be analyzed more thoroughly. This remote monitoring using the reference gas injector for analysis of operation of the gas trap ensures the efficient operation of the gas trap.

The reference gas is of a known specification and a known concentration, and can be detected by the gas analyzer. The reference gas can be argon, helium, an inert gas, or another gas. The reference gas injector can have a connector that can be fastened, such as by welding to the base manifold pipe.

A reference gas injector first pipe can fluidly communicate with the connector that is secured to the base manifold pipe. A reference gas injector elbow can fluidly connect to the reference gas injector first pipe. An injector valve, such as a ball valve, can connect to the reference gas injector elbow. The reference gas injector conduit connection can flow a reference gas into the reference gas injector.

A check valve can be located between a reference injector second pipe that can engage between the controllable valve and the reference gas injector conduit connection.

The reference gas injector can be formed of 100 percent brass, which can include all of its components other than the connector.

The conduit connection can be a nozzle, such as a barbed nozzle.

The restrictor can be an S-shaped restrictor, a U-shaped restrictor, or a shape of two inverted-U shaped conduits, which can also herein be called a double inverted U-shaped conduit.

In embodiments, the expansion chamber component can have a first coupling connected to a housing with a chamber, and a second coupling connected to the housing opposite the first coupling.

In embodiments, instead of the safety release valve, a plug can be used in place of the quick release coupling during drilling. The plug can be a bull plug.

In embodiments, each of the components of the gas trap can be removably connectable to another component of the gas trap, creating a modular unit with easy maintenance.

The controllable valve can be remotely controlled through a motor connected to a power supply and operated by a processor with data storage containing computer instructions to open and/or close the controllable valve when the processor receives signals from a controller. The controller can communicate to the processor through a network from at least one client device, such as a cellular phone.

The base manifold flow line can be made of a first elbow with a two inch conduit inner diameter connecting to a first coupling, a second elbow connecting to a third coupling, and a cross connector connecting to a second coupling.

A first base manifold segment can be disposed between the first elbow and the cross connector, and a second base manifold segment can be disposed between the second elbow and the cross connector.

A plurality of flow line pipes can be used with the base manifold. Each flow line pipe can be located between one of the plurality of couplings and one of the hammer unions. Each coupling can be welded to the flow line, and the couplings can be one piece integral collars. The well with a flow line can be a natural gas well, a geothermal well, an oil well, a water well, or combinations thereof.

Each hammer union can have a bottom hammer union pipe formed to threadably engage a top hammer union pipe. A center hammer union portion can go around and over the threadable engagement of the bottom hammer union pipe with the top hammer union pipe. Three hammer unions can be used, one on each of three pipes of the lower manifold.

The gas trap can be connected to a first network for communicating with a lap top of a user, such as an operations vice president. For example, the gas analyzer can communicate with a location processor. The location processor can have location processor data storage with at least two sets of computer instructions. The first set of computer instructions can instruct the location processor to broadcast analysis data from the gas analyzer to a web server over the first network. The second set of computer instructions in the data storage can be computer instructions to open and/or close the controllable valve when the processor receives signals from a controller through a second network.

The web server can transmit analysis data over the second network to a client device, which can be a laptop.

The client device can have a client device processor in communication with client device data storage with computer instructions to present an executive dashboard of one or a plurality of gas traps to the user. The client devices can enable the user to view multiple gas traps simultaneously at multiple locations using the executive dashboard.

The client devices can be used for receiving, viewing, and storing analysis information related to fluid from the flow line. The networks can be a satellite network, another global communication network like the Internet™, a cellular network, combinations of local area networks (LANs), wide area networks (WAN)s, or similar digital and analog networks, and can be in communication with the at least one client device.

The web server can be used in communication with at least one of the networks. The web server can be used for storing and displaying on demand analysis information related to fluid from the flow line.

The location processor with location processor data storage proximate to the gas trap can be used for storing analysis information on at least one fluid from the flow line. In embodiments, the location processor can communicate with at least one network and the web server simultaneously. The location processor data storage can contain information on fluids that can be associated with the fluid from the flow line.

In embodiments, the location processor data storage can include computer instructions to provide an alarm to hands proximate to the flow line when concentrations of components of fluid from the flow line exceed preset limits.

The location processor data storage can contain computer instructions for broadcasting analysis information on the at least one component of fluid from the flow line to displays near hands proximate to the flow line, to client devices associated with each of the hands, to client devices associated with first responders, to client devices associated with at least one user associated with the fluid of the flow line, or to combinations thereof.

The location processor can be a server, laptop, a cell phone, a personal digital assistant, a desk top computer, a right mount server, a programmable logic controller (PLC), or combinations thereof.

In embodiments, the web server can transmit analysis information through two different gateway protocols to two different networks simultaneously.

The method can use a gas analyzer that is a gas chromatograph, a continuous total gas analyzer, or another gas analyzer. The total gas can be a hydrocarbon, carbon dioxide, hydrogen sulfide, helium, hydrogen, nitrogen, oxygen, or combinations thereof.

In embodiments, the sample conditioning and filtering device (the conditioner) can remove particulates having a diameter greater than five microns.

The sample conditioning can be performed by desiccating moisture from fluid from the fluid conduit, by mist separating using a mechanical separator, by cooling fluid from the fluid conduit using a heat exchanger, by another means, or combinations thereof.

The gas trap can use tubing, such as ⅜ inch OD ¼ inch clear tubing that can be from about 50 feet to about 75 feet in length between the sample conditioning and filtering device and the gas trap for flowing fluid from the gas trap.

In embodiments, the flow of gas samples flowing through the gas trap can be reversed such that the gas trap can "blow back" the gas samples into the flow line. For example, in situations wherein the gas trap is clogged, reversing the flow of the gas samples through the gas trap can unclog the gas trap.

Reversing the flow of gas samples flowing through the gas trap can be done remotely or manually on site. A valve, such as a four way valve, can be disposed proximate the top of the gas trap.

When the four way valve is in an "off" position, the gas trap can be in fluid communication with the gas analyzer; therefore gas samples can flow from the gas trap to the gas analyzer. When the four way valve is in an "on" position the gas trap can be in fluid communication with a compressed air source. The compressed air source, when activated, can then flow compressed air into the gas trap towards the flow line; thereby unclogging the gas trap. Also, when the four way valve is in an "on" position, the gas analyzer can be in fluid communication with ambient air.

An electronic relay can be in communication with four way valve and can be programmed to turn the four way valve to an "on" and an "off" position at predefined time intervals for unclogging the gas trap. The electronic relay can be in communication with a client device through a network, such that a user can remotely turn the four way valve to an "on" and an "off" position. The electronic relay can also be manually actuated on site.

Figure 1:
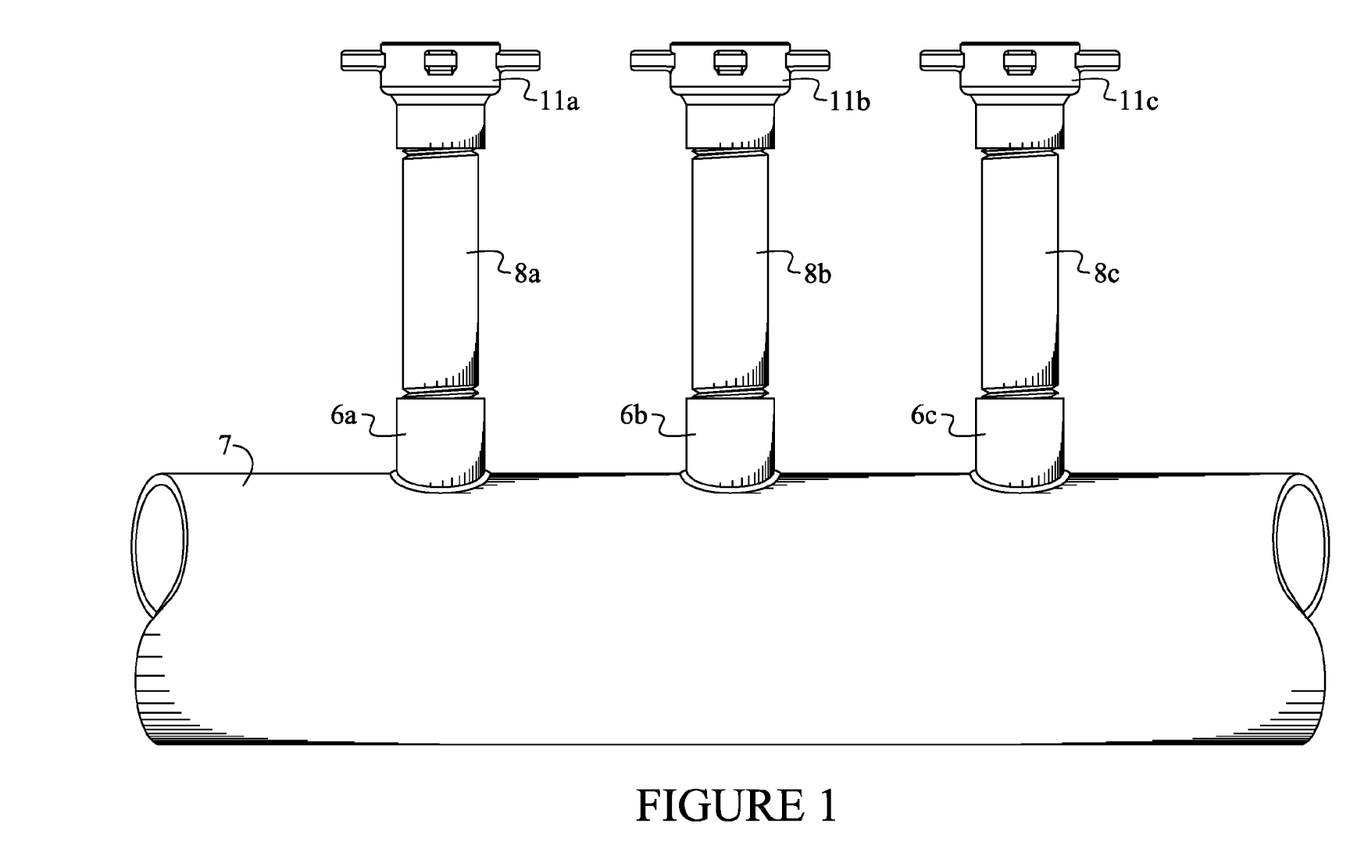
FIG. 1 is a detailed view of the couplings to the flow line.

Turning now to the Figures, FIG. 1 shows how the gas trap of the method engages a flow line.

Couplings 6a-6c are each welded to a flow line 7. In this embodiment, the couplings are two inch couplings. Coupling pipe 8a-8c each engage one of the couplings. Coupling 6c connects to coupling pipe 8c which is shown about to be engaged by a hammer unions 11c.

Figure 2:
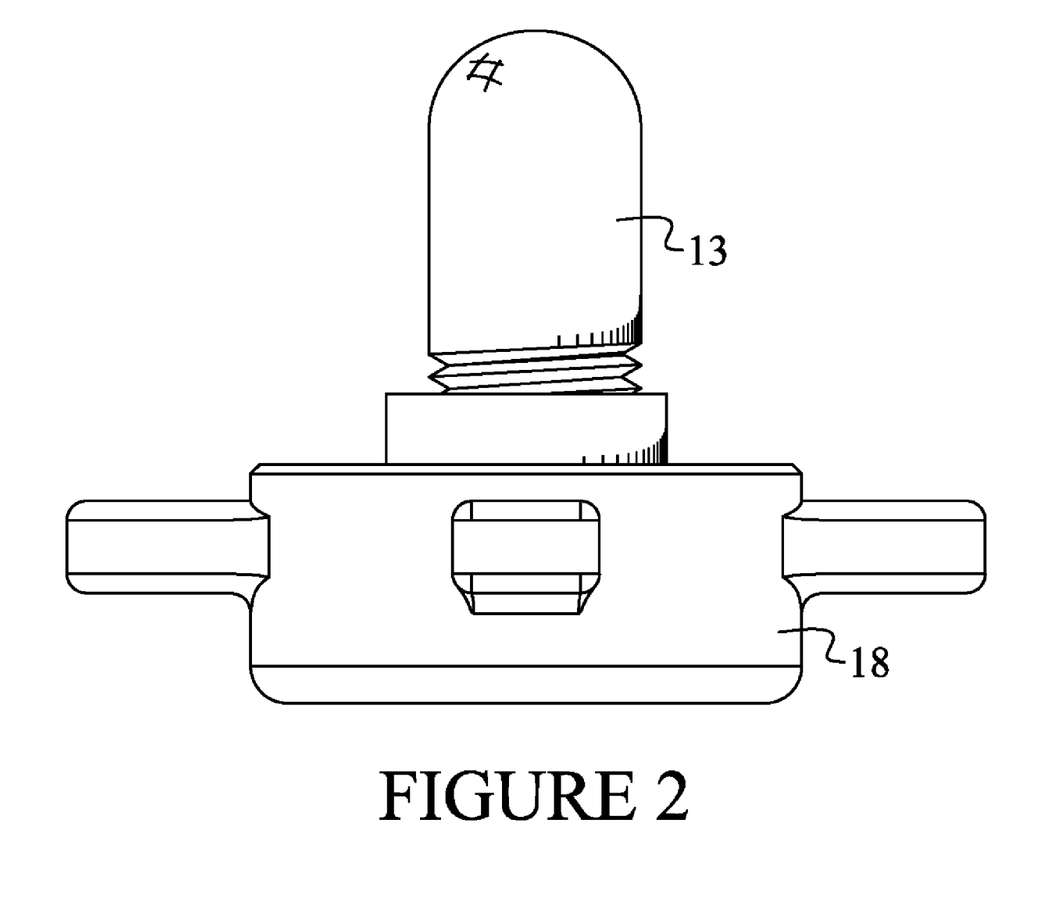
FIG. 2 is a detail of a top half of a hammer union.

FIG. 2 shows an embodiment of the top hammer union pipe 18 of hammer union 11c with a bull plug 13 connected to it.

Figure 3:
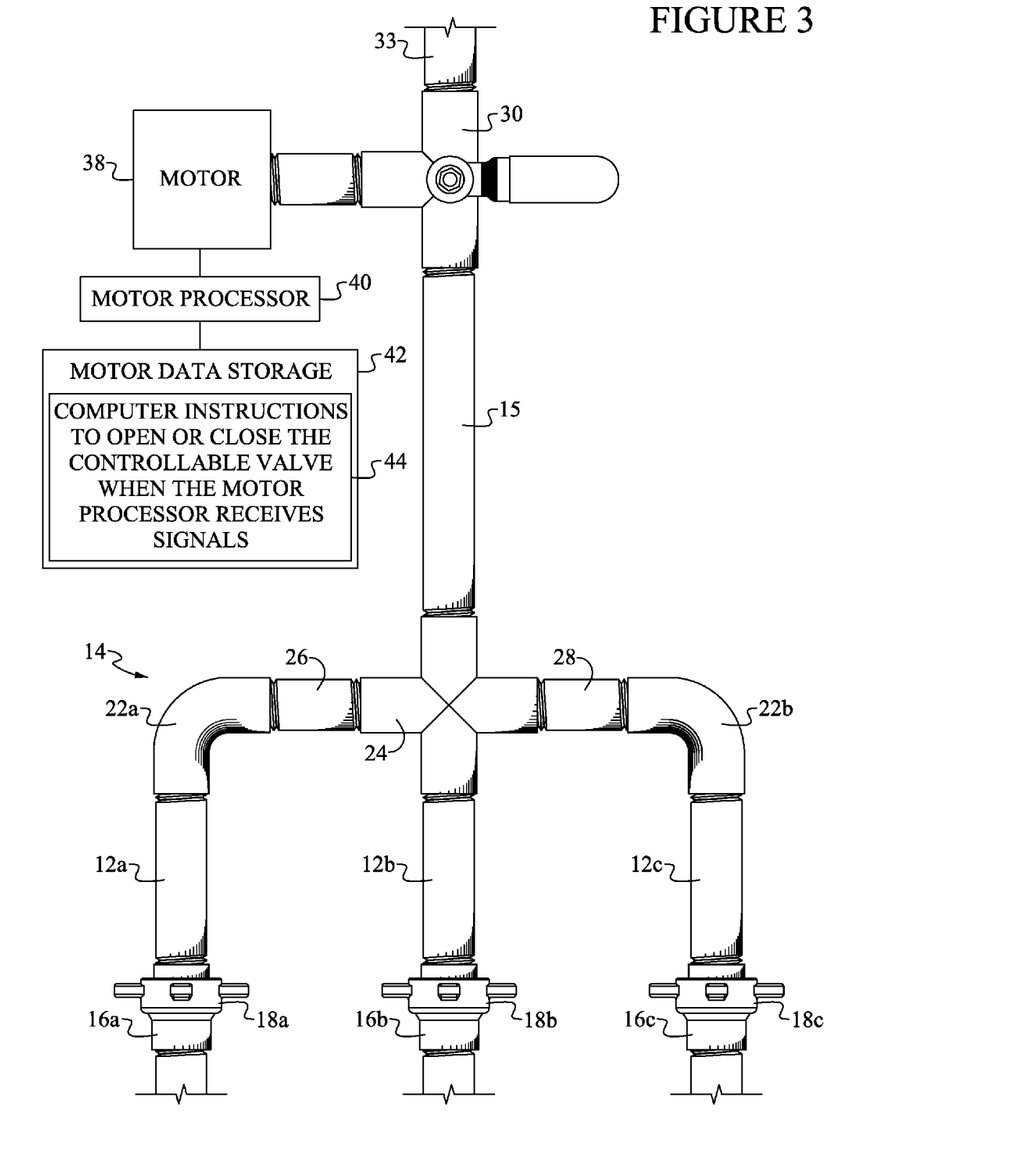
FIG. 3 is an exploded view of a bottom portion of the gas trap.

FIG. 3 shows a bottom half of the gas trap, and in particular depicts a three hammer union base manifold.

A two inch inner diameter bottom hammer union pipe 16a is shown threadably engaging the top hammer union pipe 18a. Also shown are top hammer union pipes 18b and 18c connecting to bottom hammer union pipes 16b and 16c.

To each of the top hammer union pipes are secured a base manifold pipe 12a-12c. The base manifold flow line 14 engages the three base manifold pipes simultaneously. The base manifold flow line is shown made up of a first elbow 22a that engages the first base manifold pipe 12a. A second elbow 22b engages the third base manifold pipe 12c. A cross member 24, which can have a two inch inner diameter, can both engage the first and second elbows simultaneously while engaging the second base manifold pipe 22b. The base manifold pipes can be eight inches long with a two inch inner diameter, and can threadably engage to adjoining components.

A removable and detachable first base manifold segment 26 is shown between the first elbow 22a and the cross member 24. A second base manifold segment 28 is shown between the second elbow 22b and the cross member 24, and is also removable and detachable. The base manifold segment can be two inch by four inch standard pipe segments, and can threadably engage adjoining components.

The cross member 24 connects to the chimney pipe 15. The chimney pipe can receive fluid or gas from all three hammer unions. The chimney pipe can be a two inch by three foot schedule 80 pipe.

A two inch ball valve, which can be formed of brass, can be used as the controllable valve 30. The controllable valve can be placed on the end of the chimney pipe opposite the base manifold, or in the middle of the chimney pipe, or another location. If the controllable valve is used at the very top of the chimney, another pipe segment, here shown as segment 33, can be can be connected at the top of the controllable valve. Segment 33 can be a two inch diameter by three inch long pipe segment.

Also shown in is a motor 38 in communication with the controllable valve. A motor processor 40 is shown in communication with the motor 38 and a motor data storage 42. Computer instructions 44 to open or close the controllable valve when the motor processor receives signals are shown stored in the motor data storage.

Figure 4:
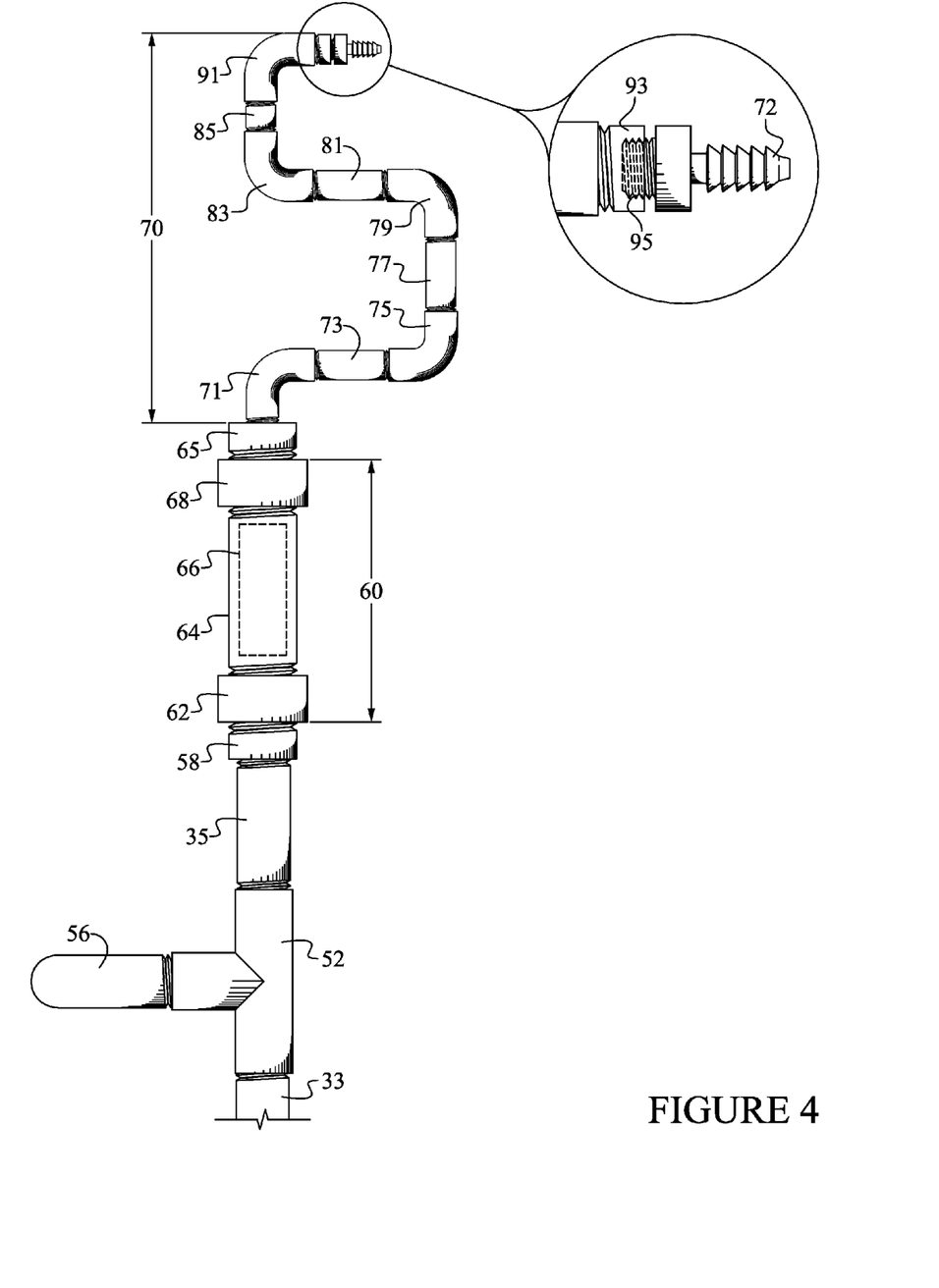
FIG. 4 is an exploded view of an upper portion of the gas trap.

FIG. 4 depicts the top half of the gas trap that connects to the bottom half shown in FIG. 3.

FIG. 4, from the bottom upwards, shows the segment 33 in fluid communication with a connector 52, shown here as a T-connector. The connector 52 is shown with a plug 56 which can be a bull plug. Other embodiments can have a safety relief valve where the bull plug is shown.

A top segment 35, which can have the same inner diameter as the connector, is shown connected to the connector 52 and to a reducer 58. The diameter of the flow from the top segment to the reducer can vary.

An expansion chamber component 60 is connected the reducer. The expansion chamber component is shown with a three inch first coupling 62 connected to a housing 64 with a chamber 66, and a second coupling 68 that is shown as a three inch coupling is connected to the housing 64 opposite the first coupling.

A bushing 65 can be used to connect the second coupling to the restrictor 70. The restrictor 70 can include a conduit connection 72 which can connect to a conduit or a hose which fluidly connects to a conditioner and then to a gas analyzer, not shown in this Figure. The conduit connection is shown as a barbed nozzle.

The restrictor 70 can be formed from a plurality of removable, re-engagable, and threadably engagable components. A first restrictor elbow 71 can connect to a 1 inch by 4 inch first restrictor pipe segment 73. A second restrictor elbow 75 can connect to the first restrictor pipe segment 73 and to a second restrictor pipe segment 77. The second restrictor pipe segment 77 can be a 1 inch by 4 inch standard pipe segment. A third restrictor elbow 79 can connect at about a 90 degree angle to the second restrictor pipe segment 77. The third restrictor elbow 79 can threadably engage the other adjoining segments. The third restrictor elbow 79 can be a 1 inch diameter elbow shaped pipe segment and can be connected to a third restrictor pipe segment 81 which can have a 1 inch diameter and a 4 inch length. A fourth restrictor elbow 83 can connect to the third restrictor pipe segment 81 and to a ¼ inch diameter standard nipple 85. The nipple 85 can engage a fifth restrictor elbow 91 which can in-turn engage another fitting 93. Also shown is a detail of the fitting 93 with ¼ inch female pipe threads 95.

Figure 5:
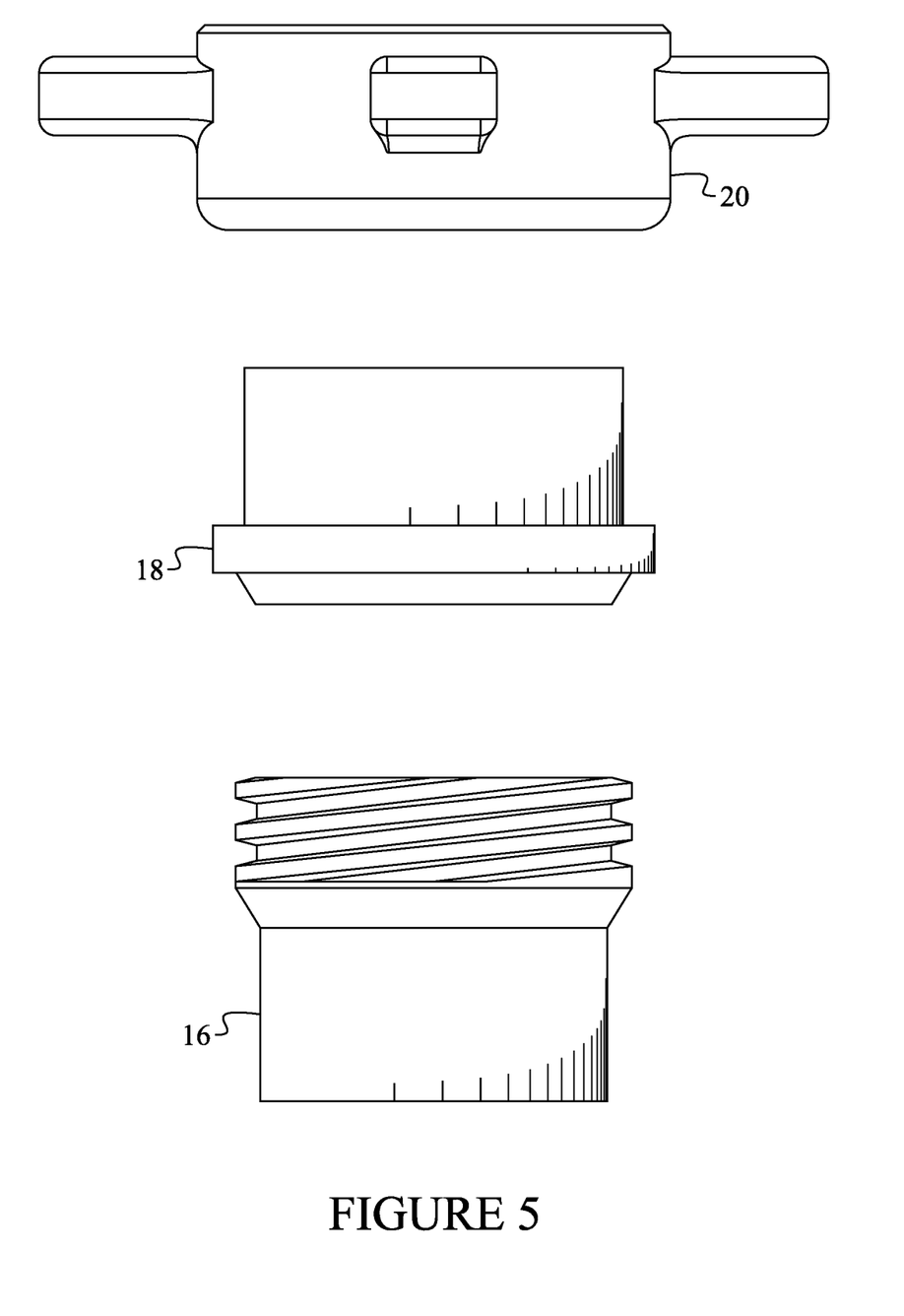
FIG. 5 is an exploded view of a hammer union.

FIG. 5 shows the union hammer in an exploded view with the bottom hammer union pipe 16, the top hammer union pipe 18, and the center hammer union portion 20 that covers the threaded engagement of the top and the bottom union pipes.

Figure 6:
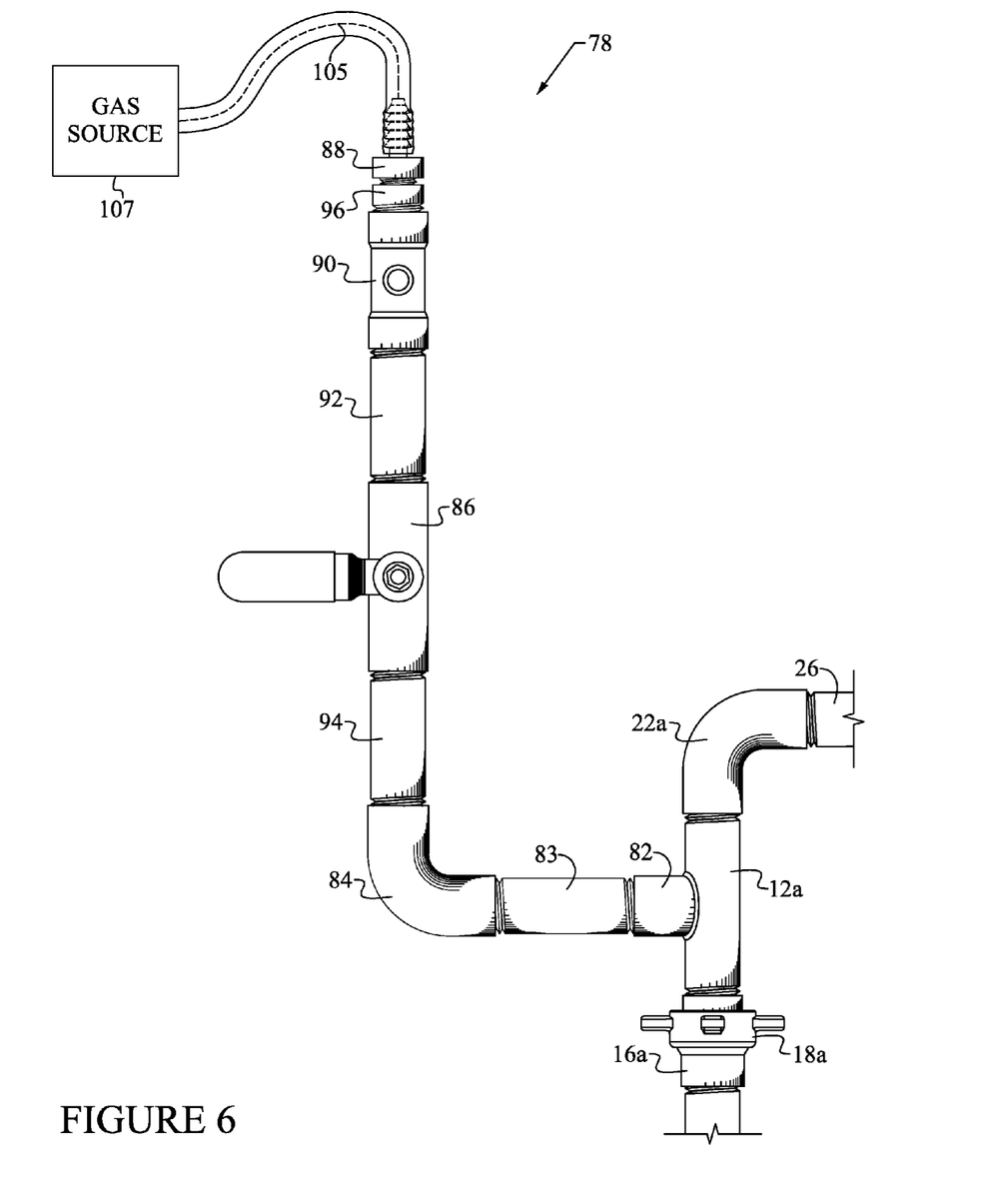
FIG. 6 is an exploded view of a reference gas injector usable in the method.

FIG. 6 shows an exploded view of the reference gas injector 78, which can be welded to the base manifold pipe 12a. The reference gas injector can be disposed at an angle from about 10 degrees to about 90 degrees from the base manifold pipe.

A thread-o-let 82, which can be another type of connector, can be welded to the base manifold pipe. The thread-o-let is shown threadably secured to a reference gas injector first pipe 83. The first pipe 83 can have an inner diameter of ¼ inch, as would the connector 82. The first pipe can have a length of 1 and ½ inches. The first pipe is shown threadably connected an injector elbow 84. A second pipe 92 can be connected to the injector elbow; however, in the embodiment shown, a third pipe 94 is inserted between the injector elbow and the second pipe 92. A ball valve 86 is disposed between the injector elbow and the second pipe to assist in the installation of the reference gas injector.

A check valve 90 is disposed between the second pipe and a nozzle 88 for introducing reference gas 105 from a gas source 107.

A reference gas injector bushing 96 is shown between the nozzle and the check valve. The nozzle can be a $\frac{1}{8}^{th}$ inch×¼ inch barbed brass nozzle, or can be any type of hose attachment. The bushing can be a ¼ mpt×$\frac{1}{8}^{th}$ inch fpt brass bushing.

Also shown are bottom hammer union pipe 16a, top hammer union pipe 18a, first base manifold segment 26, and first elbow 22a.

Figure 7:
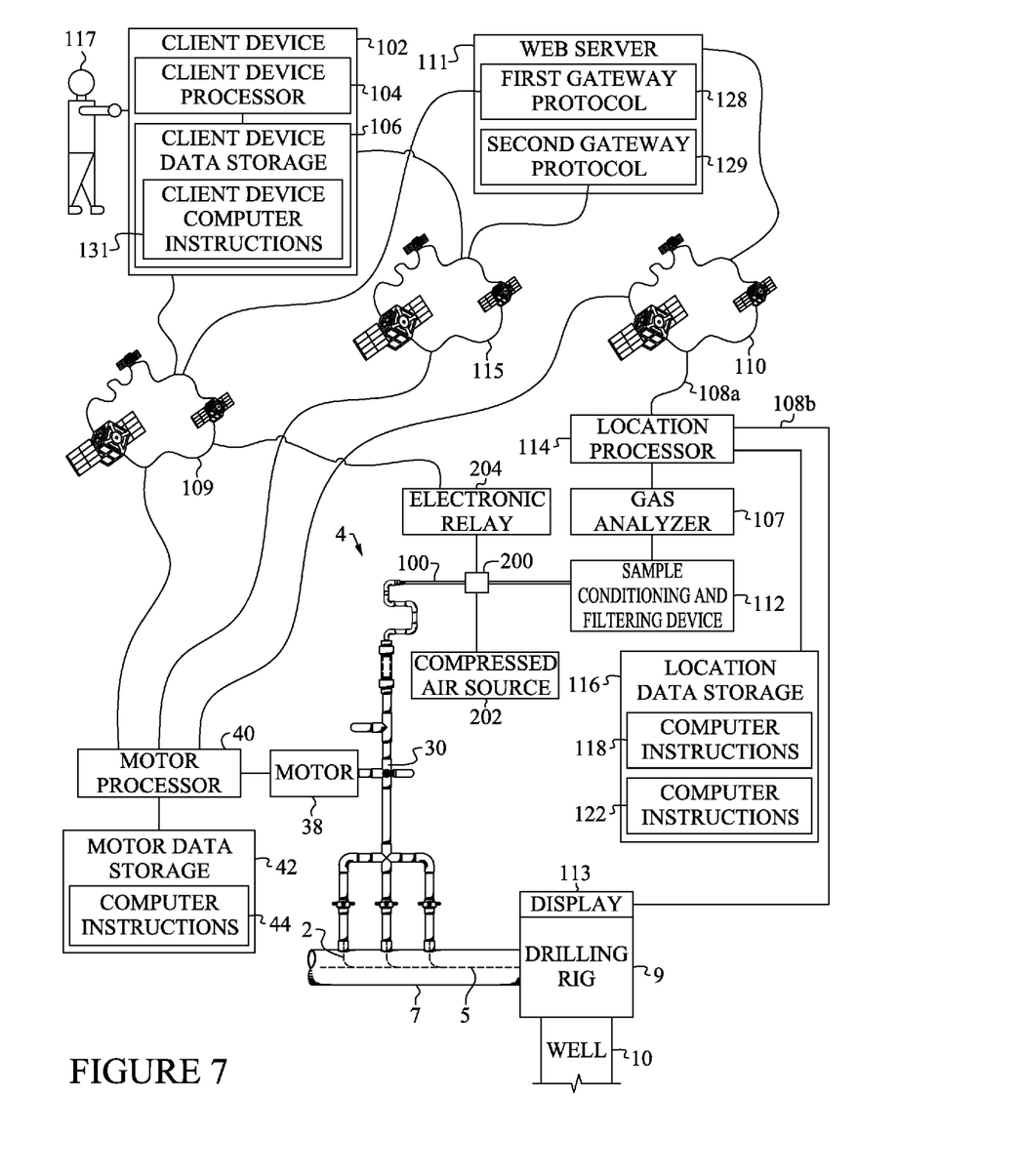
FIG. 7 is a diagram of a gas trap in communication with a network usable in the method.

FIG. 7 shows a diagram of the gas trap which can be connected to the Internet for communicating with a lap top of a user or client, such as an operations vice president.

The gas trap 4 is fluidly connected to a flow line 7 that contains fluid 5 from a drilling rig 9 of a well 10.

The gas trap captures gas samples 2 from the flow line. The gas trap is shown connected by a tubing 100 to a sample conditioning and filtering device 112 that removes moisture from the gas sampled by the gas trap.

The sample conditioning and filtering device can then feed conditioned sample gas to a gas analyzer 107 that communicates to a location processor 114. The location processor is in communication with location data storage 116 with computer instructions. The location data storage can have computer instructions 118 to broadcast gas analysis data 108a from the gas analyzer to a web server 111 over a first network 110 and/or to broadcast gas analysis data 108b to a display 113 proximate the hands. The location data storage can have computer instructions 122 to provide an alarm when concentrations of components of the gas sample exceed preset limits.

The web server can transmit the analysis data over a second network 109 to a client device 102, which can be a laptop.

The client device can have a client device processor 104, which can be in communication with a client device data storage 106 with client device computer instructions 131 to present an executive dashboard of one or a plurality of gas traps to the user 117. The client device can enable a user to view simultaneously multiple gas traps at multiple locations using the executive dashboard.

A motor 38 is shown in communication with the controller valve 30. The motor is also shown in communication with a motor processor 40 which is in-turn can be in communication with a motor data storage 42. The motor data storage has computer instructions 44 to open or close the controllable valve when the motor processor receives signals, such as from a client device. The motor processor is shown in communication with the first 110, the second 109, and a third network 115.

The web server is also shown in communication with the third network which is also in communication with the client device. The web server can simultaneously transmit analysis information through a first gateway protocol 128 and a second gateway protocol 129 to the second and third networks respectively. The two gateway protocols can be two different gateway protocols.

Also shown is a four way valve 200 in communication with the gas trap and the sample and conditioning device 112 along the tubing 100.

A compressed air source 202 is shown in fluid communication with four way valve.

An electronic relay 204 is shown in communication with the four way valve for actuating the four way valve between an "on" and "off" position. The electronic relay is shown in communication with the client device through the first network, allowing a user to remotely actuate the four way valve between the "on" and "off" positions.

FIG. 8A-8D shows a flow chart of an embodiment of the present method.

Figure 8A:
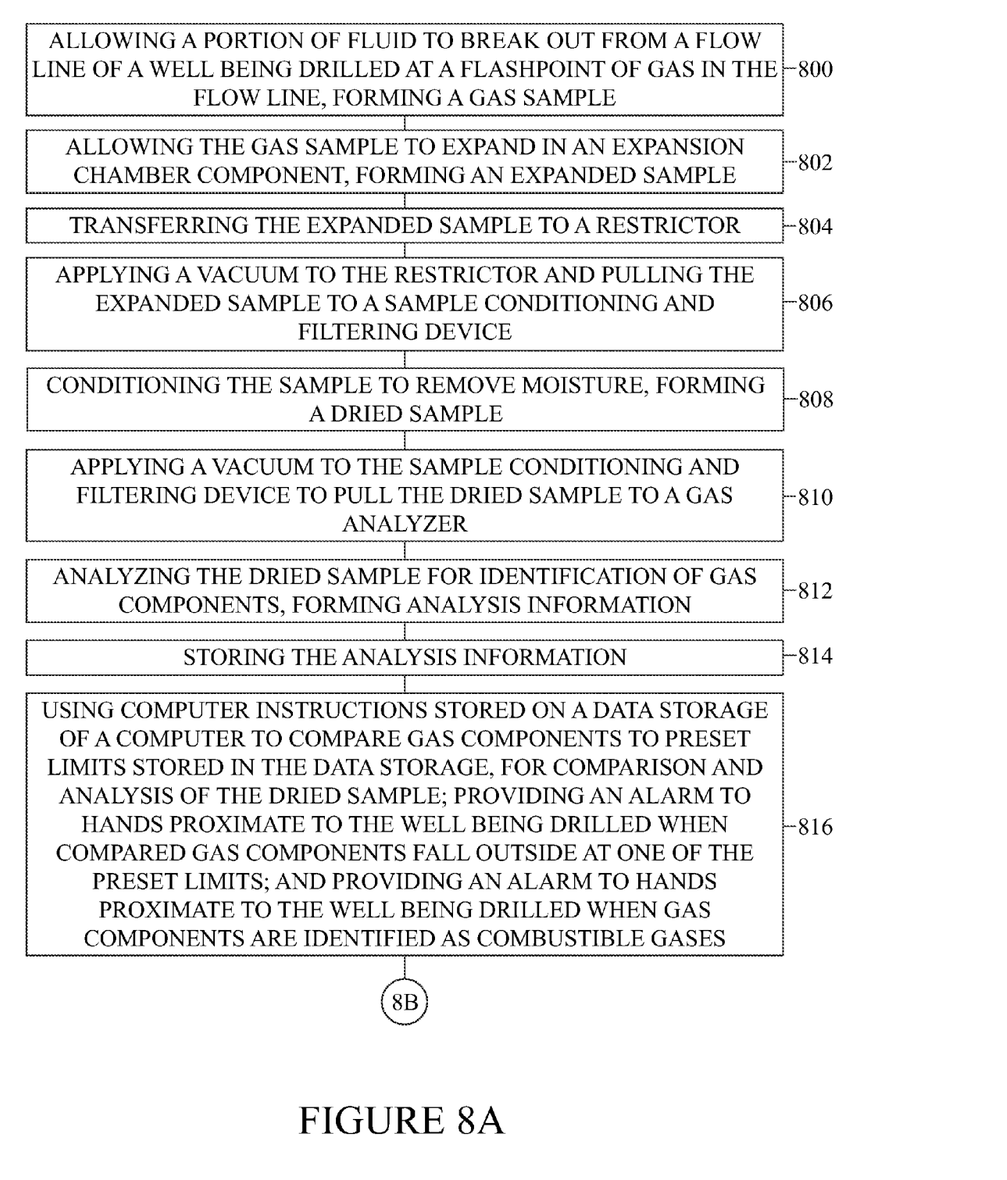
FIGS. 8A-8D is a flow chart of an embodiment of the method.

Step 800 includes allowing a portion of fluid to break out from a flow line of a well being drilled at a flashpoint of gas in the flow line, forming a gas sample.

Step 802 includes allowing the gas sample to expand in an expansion chamber component, forming an expanded sample.

Step 804 includes transferring the expanded sample to a restrictor.

Step 806 includes applying a vacuum to the restrictor and pulling the expanded sample to a sample conditioning and filtering device.

Step 808 includes conditioning the sample to remove moisture, forming a dried sample.

Step 810 includes applying a vacuum to the sample conditioning and filtering device to pull the dried sample to a gas analyzer.

Step 812 includes analyzing the dried sample for identification of gas components, forming analysis information.

Step 814 includes storing the analysis information.

Embodiments of the method can also include the following steps.

Figure 8B:
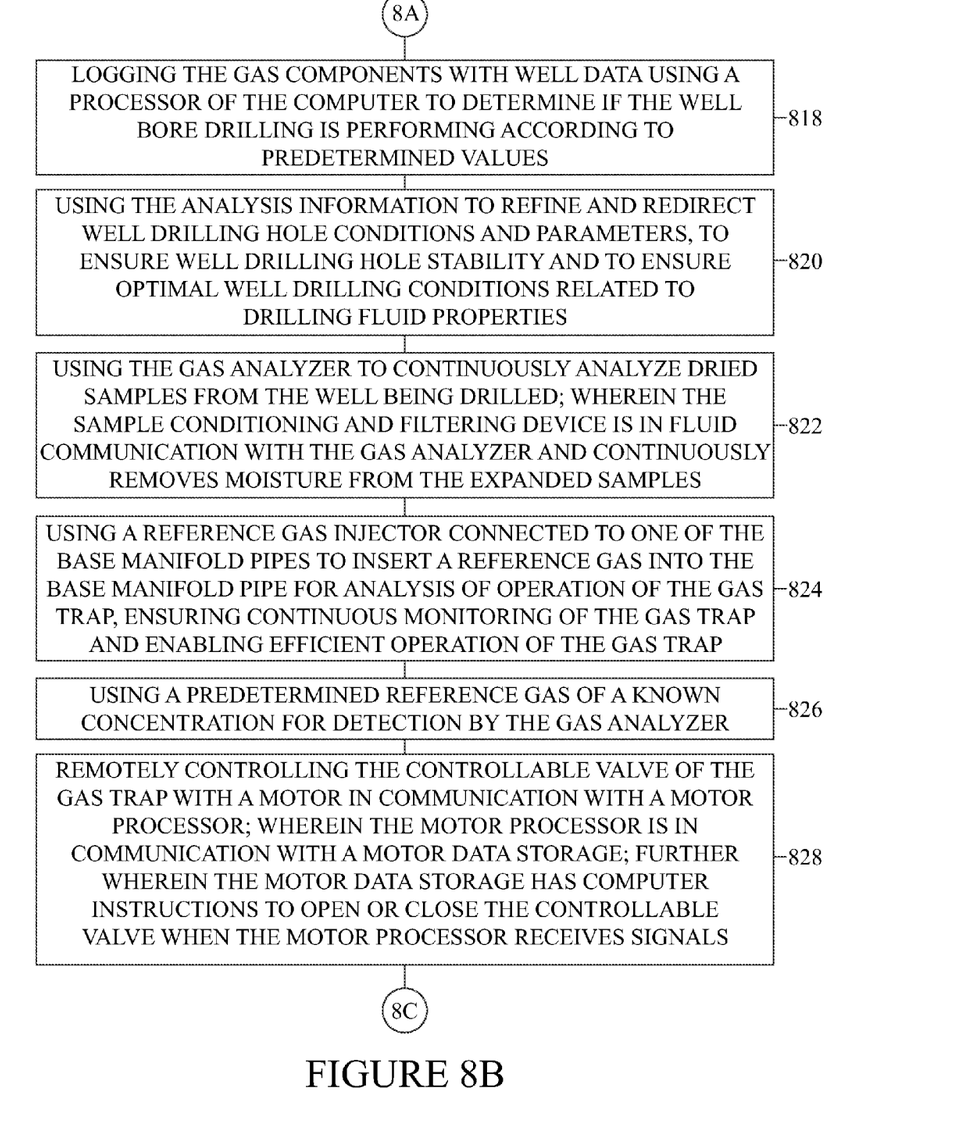

Step 816 includes using computer instructions stored on a data storage of a computer to compare gas components to preset limits stored in the data storage, for comparison and analysis of the dried sample; providing an alarm to hands proximate to the well being drilled when compared gas components fall outside at one of the preset limits; and providing an alarm to hands proximate to the well being drilled when gas components are identified as combustible gases.

Step 818 includes logging the gas components with well data using a processor of the computer to determine if the well bore drilling is performing according to predetermined values.

Step 820 includes using the analysis information to refine and redirect well drilling hole conditions and parameters, to ensure well drilling hole stability and to ensure optimal well drilling conditions related to drilling fluid properties.

Step 822 includes using the gas analyzer to continuously analyze dried samples from the well being drilled; wherein the sample conditioning and filtering device is in fluid communication with the gas analyzer and continuously removes moisture from the expanded samples.

Step 824 includes using a reference gas injector connected to one of the base manifold pipes to insert a reference gas into the base manifold pipe for analysis of operation of the gas trap, ensuring continuous monitoring of the gas trap and enabling efficient operation of the gas trap.

Step 826 includes using a predetermined reference gas of a known concentration for detection by the gas analyzer.

Step 828 includes remotely controlling the controllable valve of the gas trap with a motor in communication with a motor processor; wherein the motor processor is in communication with a motor data storage; further wherein the motor data storage has computer instructions to open or close the controllable valve when the motor processor receives signals.

Step 830 includes remotely controlling the motor processor through a network using a client device; wherein the client device sends signals to the motor processor over the network to open or close the controllable valve.

Figure 8C:
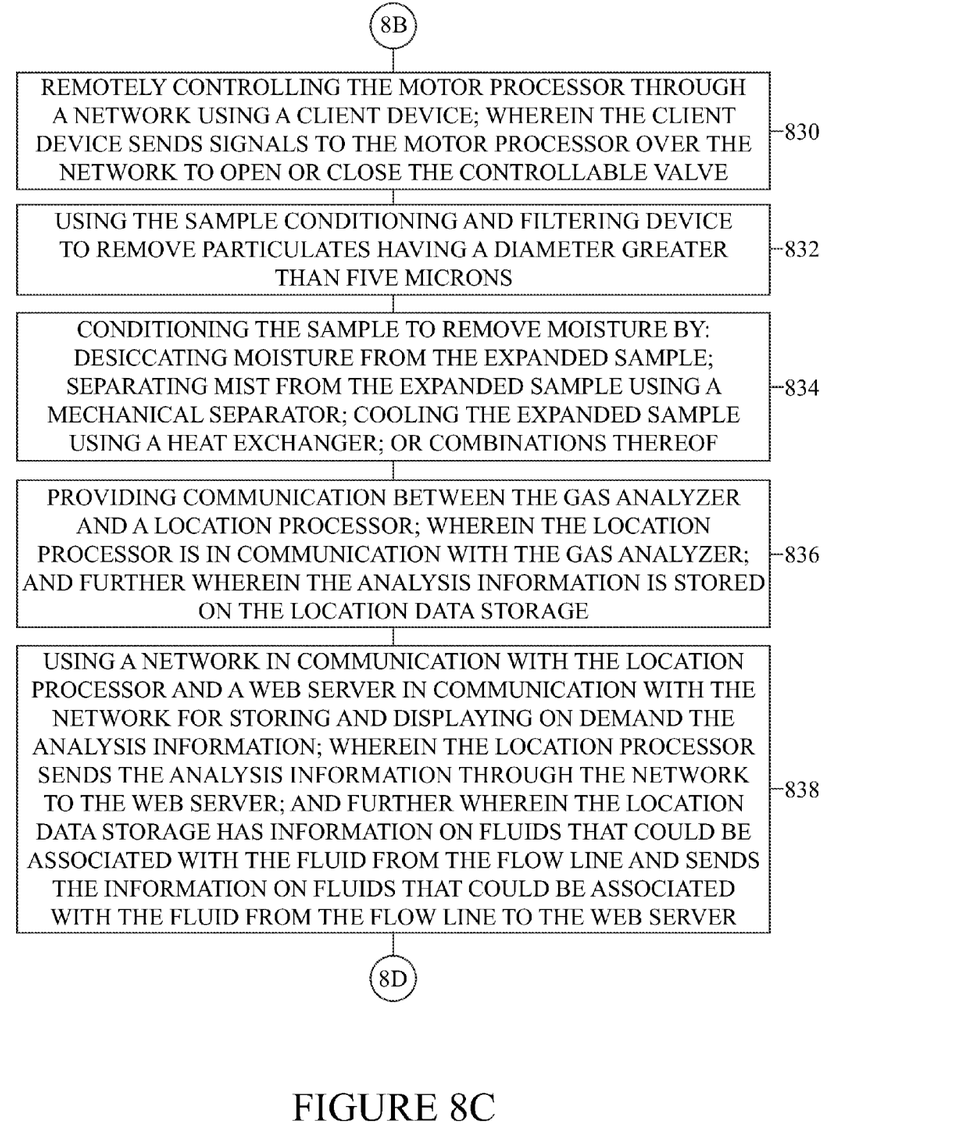

Step 832 includes using the sample conditioning and filtering device to remove particulates having a diameter greater than five microns.

Step 834 includes conditioning the sample to remove moisture by: desiccating moisture from the expanded sample; separating mist from the expanded sample using a mechanical separator; cooling the expanded sample using a heat exchanger; or combinations thereof.

Step 836 includes providing communication between the gas analyzer and a location processor; wherein the location processor is in communication with the gas analyzer; and further wherein the analysis information is stored on the location data storage.

Step 838 includes using a network in communication with the location processor and a web server in communication with the network for storing and displaying on demand the analysis information; wherein the location processor sends the analysis information through the network to the web server; and further wherein the location data storage has information on fluids that could be associated with the fluid from the flow line and sends the information on fluids that could be associated with the fluid from the flow line to the web server.

Step 840 includes using the location processor and computer instructions on the location data storage to provide an alarm to hands proximate to the flow line when concentrations of components of fluid from the flow line exceed preset limits.

Step 842 includes using a client device having a client processor and client data storage for receiving, viewing and storing analysis information; wherein the client device is in communication with the network.

Step 844 includes using the location processor and computer instructions on the location data storage to broadcast analysis information to a member of the group consisting of: displays near hands proximate to the flow line; client devices associated with each of the hands; client devices associated with first responders; client devices associated with at least one user associated with the fluid of the flow line; or combinations thereof.

Figure 8D:
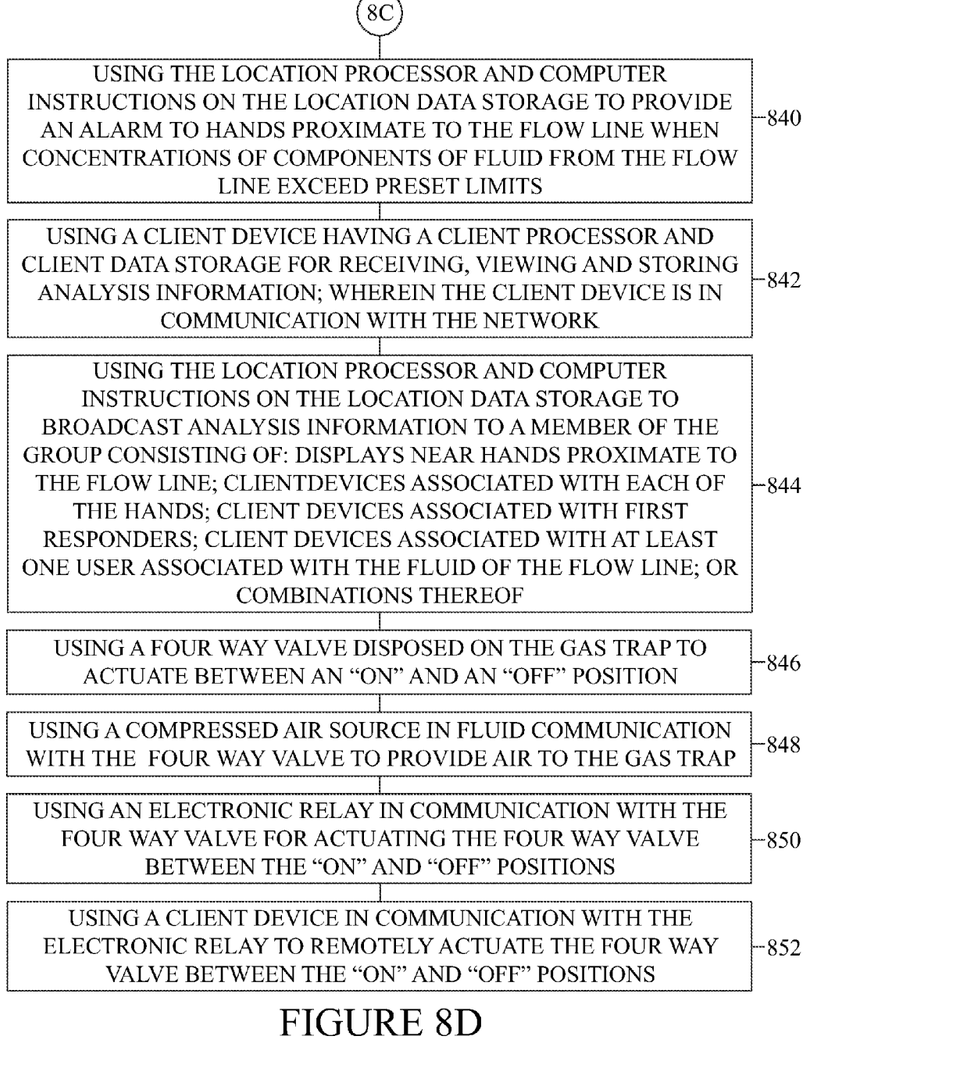

Step 846 can include using a four way valve disposed on the gas trap to actuate between an "on" and an "off" position.

Step 848 can include using a compressed air source in fluid communication with the four way valve to provide air to the gas trap.

Step 850 can include using an electronic relay in communication with the four way valve for actuating the four way valve between the "on" and "off" positions.

Step 852 can include using a client device in communication with the electronic relay to remotely actuate the four way valve between the "on" and "off" positions.

While these embodiments have been described with emphasis on the embodiments, it should be understood that within the scope of the appended claims, the embodiments might be practiced other than as specifically described herein.

What is claimed is:

1. A method for analyzing fluid from a flow line associated with a well being drilled, the method comprising:
    a. allowing a portion of fluid to break out from a flow line of a well being drilled at a flashpoint of gas in the flow line forming a gas sample;
    b. allowing the gas sample to expand in an expansion chamber component forming an expanded sample;
    c. transferring the expanded sample to a restrictor;
    d. applying a vacuum to the restrictor and pulling the expanded sample to a sample conditioning and filtering device;
    e. conditioning the sample to remove moisture, forming a dried sample;
    f. applying a vacuum to the sample conditioning and filtering device to pull the dried sample to a gas analyzer;

g. analyzing the dried sample for identification of gas components, forming analysis information; and h. storing the analysis information.

2. The method of claim 1, further comprising the steps of:

a. using computer instructions stored on a data storage of a computer to compare gas components to preset limits stored in the data storage, for comparison and analysis of the dried sample;

b. providing an alarm to hands proximate to the well being drilled when compared gas components fall outside at one of the preset limits; and c. providing an alarm to hands proximate to the well being drilled when gas components are identified as combustible gases.

3. The method of claim 2, wherein the gas components are logged with well data using a processor of the computer to determine if the well bore drilling is performing according to predetermined values.

4. The method of claim 1, further comprising the step of using the analysis information to refine and redirect well drilling hole conditions and parameters, to ensure well drilling hole stability and to ensure optimal well drilling conditions related to drilling fluid properties.

5. The method of claim 1, wherein the gas analyzer continuously analyzes dried samples from the well being drilled; and further wherein the sample conditioning and filtering device is in fluid communication with the gas analyzer and continuously removes moisture from the expanded samples.

6. The method of claim 1, wherein the gas trap comprises:

a. a plurality of couplings connected in parallel; wherein each coupling secures to a flow line of a drilling rig for a well;

b. a plurality of hammer unions; wherein each hammer union engages one of the couplings;

c. a plurality of base manifold pipes; wherein each base manifold pipe engages one of the hammer unions;

d. a base manifold flow line for flowing gas samples from each of the couplings to a chimney pipe;

e. a controllable valve in communication with the chimney pipe;

f. a connector integral with the chimney pipe, for providing a pressure safety release;

g. a reducer in fluid communication with the chimney opposite the base manifold flow line, for modifying the diameter of gas samples flowing from the flow line;

h. an expansion chamber component in fluid communication with the reducer having an expansion chamber diameter greater than the reducer diameter;

i. a restrictor in fluid communication with the expansion chamber component opposite the reducer; wherein the restrictor has a diameter no more than one third the expansion chamber diameter; and j. a conduit connection in fluid communication with the restrictor for engaging a conduit.

7. The method of claim 6, further comprising the step of using a reference gas injector connected to one of the base manifold pipes to insert a reference gas into the base manifold pipe for analysis of operation of the gas trap, ensuring continuous monitoring of the gas trap and enabling efficient operation of the gas trap.

8. The method of claim 7, further comprising using a predetermined reference gas of a known concentration for detection by the gas analyzer.

9. The method of claim 7, further comprising using a check valve with the reference injector for safety.

10. The method of claim 1, further comprising using as the restrictor a member of the group consisting of: an S-shaped restrictor, a U-shaped restrictor, or a double inverted U-shaped restrictor.

11. The method of claim 1, further comprising using as the restrictor an undulating shaped restrictor with at least two turns as the gas sample passes from the couplings to the conduit connector, allowing for reduction of pressure of the gas sample.

12. The method of claim 1, further comprising the step of remotely controlling the controllable valve of the gas trap with a motor in communication with a motor processor; wherein the motor processor is in communication with a motor data storage; further wherein the motor data storage has computer instructions to open or close the controllable valve when the motor processor receives signals.

13. The method of claim 12, further comprising remotely controlling the motor processor through a network using a client device; wherein the client device sends signals to the motor processor over the network to open or close the controllable valve.

14. The method of claim 1, wherein is a member of the group consisting of: a natural gas well; a geothermal well; an oil well; a water well; or combinations thereof is being drilled as the well.

15. The method of claim 1, wherein the step of analyzing the dried sample performed using a gas chromatograph or a continuous total gas analyzer.

16. The method of claim 15, wherein the total gas is a selected from the group consisting of: hydrocarbon, carbon dioxide, hydrogen sulfide, helium, hydrogen, nitrogen, oxygen, or combinations thereof.

17. The method of claim 1, further comprising the step of sample conditioning and filtering to remove particulates having a diameter greater than five microns.

18. The method of claim 17, wherein the step of conditioning the sample to remove moisture is performed by: comprises:

a. desiccating moisture from the expanded sample;

b. separating mist from the expanded sample using a mechanical separator;

c. cooling the expanded sample using a heat exchanger; or d. combinations thereof.

19. The method of claim 1, wherein the gas analyzer is in communication with a location processor, the location processor is in communication with the gas analyzer, and further wherein the analysis information is stored on the location data storage.

20. The method of claim 19, wherein a server, laptop, a cell phone, a personal digital assistant, a computer, a right mount server, a programmable logic controller, or combinations thereof is used as the location processor.

21. The method of claim 19, further comprising using a network in communication with the location processor and a web server in communication with the network for storing and displaying on demand the analysis information; wherein the location processor sends the analysis information through the network to the web server; and further wherein the location data storage has information on fluids that could be associated with the fluid from the flow line and sends the information on fluids that could be associated with the fluid from the flow line to the web server.

22. The method of claim 21, wherein a local area network, a cellular network, a satellite network, a global communication network, or combinations thereof is used as the location network.

23. The method of claim 21, further comprising using the location processor and computer instructions on the location data storage to provide an alarm to hands proximate to the flow line when concentrations of components of fluid from the flow line exceed preset limits.

24. The method of claim 23, further comprising using a client device having a client processor and client data storage for receiving, viewing and storing analysis information; wherein the client device is in communication with the network.

25. The method of claim 24, further comprising using the location processor and computer instructions on the location data storage to broadcast analysis information to a member of the group consisting of: displays near hands proximate to the flow line; client devices associated with each of the hands; client devices associated with first responders; client devices associated with at least one user associated with the fluid of the flow line; or combinations thereof.

26. The method of claim 1, further comprising the step of:
a. using a four way valve disposed on the gas trap to actuate between an "on" and an "off" position, wherein the gas trap and the gas analyzer are in fluid communication with the four way valve; and
b. using a compressed air source in fluid communication with the four way valve to provide air to the gas trap; wherein when the four way valve is in the "off" position the gas trap is in fluid communication with the gas analyzer and when the four way valve is in the "on" position the compressed air source is in fluid communication with the gas trap for providing the air to the gas trap.

27. The method of claim 26, further comprising the step of using an electronic relay in communication with the four way valve for actuating the four way valve between the "on" and "off" positions.

28. The method of claim 27, further comprising the step using a client device in communication with the electronic relay to remotely actuate the four way valve between the "on" and "off" positions.

* * * * *